US009486200B2

United States Patent
Melsheimer et al.

(10) Patent No.: US 9,486,200 B2
(45) Date of Patent: Nov. 8, 2016

(54) ABDOMINAL RETRACTOR

(71) Applicant: Cook Medical Technologies LLC, Bloomington, IN (US)

(72) Inventors: Jeffry S. Melsheimer, Springville, IN (US); Leslie Cook, Indianapolis, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 307 days.

(21) Appl. No.: 14/150,866

(22) Filed: Jan. 9, 2014

(65) Prior Publication Data

US 2014/0194698 A1 Jul. 10, 2014

Related U.S. Application Data

(60) Provisional application No. 61/750,395, filed on Jan. 9, 2013.

(51) Int. Cl.
*A61B 1/32* (2006.01)
*A61B 17/02* (2006.01)
*A61B 17/00* (2006.01)

(52) U.S. Cl.
CPC ....... *A61B 17/0293* (2013.01); *A61B 17/0218* (2013.01); *A61B 17/0281* (2013.01); *A61B 2017/00862* (2013.01); *A61B 2017/0225* (2013.01)

(58) Field of Classification Search
CPC .... A61B 1/32; A61B 17/02; A61B 17/0218; A61B 17/0281; A61B 17/0293; A61B 2017/0225; A61B 2017/0287
USPC .................................................. 600/201–249
See application file for complete search history.

(56) References Cited

U.S. PATENT DOCUMENTS

| 1,947,649 | A | * | 2/1934 | Kadavy | A61B 17/0293 600/203 |
| 2,671,444 | A | * | 3/1954 | Pease, Jr. | A61F 2/0063 606/151 |
| 3,054,406 | A | * | 9/1962 | Usher | A61B 19/00 139/426 R |

(Continued)

FOREIGN PATENT DOCUMENTS

WO  WO 2013/009795 A1  1/2013

OTHER PUBLICATIONS

International Search Report and Written Opinion issued in PCT/US2014/010790, dated Jun. 6, 2014, 20 pgs.

*Primary Examiner* — Christian Sevilla
*Assistant Examiner* — Eric S Gibson
(74) *Attorney, Agent, or Firm* — Woodard, Emhardt, Moriarty, McNett & Henry LLP

(57) ABSTRACT

Devices and methods for retracting tissue, such as bowels and organs, within the body of a patient are generally disclosed. In particular, the present disclosure describes surgical retractors having a series of intersecting strands defining openings there between, wherein the openings are enlargeable by slidable passage of the strands relative to one another. The present disclosure also teaches surgical retractors having a frame that defines a central opening and a supporting structure extending across the central opening and defining a plurality of openings, wherein the frame extends through the openings. In some embodiments, a surgical retractor comprises a monolithic polymeric structure extending across the central opening defined by a frame. Other embodiments and methods are disclosed.

20 Claims, 12 Drawing Sheets

(56) References Cited

U.S. PATENT DOCUMENTS

| | | | | |
|---|---|---|---|---|
| 3,124,136 A * | 3/1964 | Usher | A61F 2/0063 | 606/213 |
| 3,983,863 A * | 10/1976 | Janke | A61B 17/02 | 600/37 |
| 4,190,042 A * | 2/1980 | Sinnreich | A61B 17/0218 | 600/204 |
| 4,347,847 A * | 9/1982 | Usher | A61F 2/0063 | 128/898 |
| 4,655,221 A * | 4/1987 | Devereux | A61F 2/0063 | 606/151 |
| 4,693,720 A * | 9/1987 | Scharnberg | A61F 2/0063 | 427/2.24 |
| 4,839,215 A * | 6/1989 | Starling | A61C 8/0012 | 428/131 |
| 4,973,300 A * | 11/1990 | Wright | A61B 19/00 | 600/37 |
| 4,990,163 A * | 2/1991 | Ducheyne | A61F 2/30767 | 204/491 |
| 5,141,515 A * | 8/1992 | Eberbach | A61B 17/0057 | 128/887 |
| 5,159,921 A * | 11/1992 | Hoover | A61B 17/0293 | 600/205 |
| 5,308,327 A * | 5/1994 | Heaven | A61B 17/00234 | 604/103.09 |
| 5,334,217 A * | 8/1994 | Das | A61B 17/0057 | 606/151 |
| 5,337,754 A * | 8/1994 | Heaven | A61B 17/00234 | 128/DIG. 24 |
| 5,366,460 A * | 11/1994 | Eberbach | A61B 17/0057 | 128/887 |
| 5,368,602 A * | 11/1994 | de la Torre | A61B 17/0057 | 602/44 |
| 5,443,499 A * | 8/1995 | Schmitt | A61F 2/06 | 623/1.13 |
| 5,486,182 A * | 1/1996 | Nakao | A61B 17/32056 | 600/37 |
| 5,569,273 A * | 10/1996 | Titone | A61F 2/0063 | 442/1 |
| 5,954,767 A * | 9/1999 | Pajotin | A61F 2/0063 | 606/215 |
| 6,022,376 A * | 2/2000 | Assell | A61F 2/441 | 623/17.12 |
| 6,071,291 A * | 6/2000 | Forst | A61B 17/8085 | 606/151 |
| 6,129,755 A * | 10/2000 | Mathis | A61F 2/91 | 623/1.15 |
| 6,162,172 A * | 12/2000 | Cosgrove | A61B 17/0293 | 600/208 |
| 6,214,020 B1 * | 4/2001 | Mulhauser | A61F 2/0063 | 606/151 |
| 6,216,698 B1 * | 4/2001 | Regula | A61F 6/08 | 128/830 |
| 6,221,100 B1 * | 4/2001 | Strecker | A61F 2/90 | 623/1.22 |
| 6,267,772 B1 * | 7/2001 | Mulhauser | A61F 2/0063 | 606/151 |
| 6,270,530 B1 * | 8/2001 | Eldridge | A61F 2/0063 | 600/37 |
| 6,391,060 B1 * | 5/2002 | Ory | A61F 2/0063 | 606/151 |
| 6,416,459 B1 * | 7/2002 | Haindl | A61F 2/2481 | 600/37 |
| 6,443,964 B1 * | 9/2002 | Ory | A61F 2/0063 | 606/151 |
| 6,450,983 B1 * | 9/2002 | Rambo | A61B 17/0293 | 600/206 |
| 6,482,146 B1 * | 11/2002 | Alferness | A61F 2/2481 | 600/37 |
| 6,620,098 B1 * | 9/2003 | Milverton | A61B 17/0231 | 600/208 |
| 6,902,530 B1 * | 6/2005 | Pianka | A61B 1/00142 | 600/220 |
| 6,998,165 B2 * | 2/2006 | Howland | B32B 5/26 | 428/105 |
| 7,112,172 B2 * | 9/2006 | Orban, III | A61B 17/0218 | 600/204 |
| 7,341,601 B2 * | 3/2008 | Eisermann | A61B 17/68 | 623/17.11 |
| 7,452,371 B2 * | 11/2008 | Pavcnik | A61F 2/01 | 623/1.24 |
| 7,670,366 B2 * | 3/2010 | Case | A61F 2/2418 | 623/1.13 |
| 7,946,236 B2 * | 5/2011 | Butcher | D05C 17/00 | 112/157 |
| 8,074,591 B2 * | 12/2011 | Butcher | D05C 7/00 | 112/475.18 |
| 8,114,018 B2 * | 2/2012 | Park | A61B 17/02 | 600/206 |
| 8,128,559 B2 * | 3/2012 | Minnelli | A61B 17/0218 | 600/205 |
| 8,133,255 B2 * | 3/2012 | Ravikumar | A61B 17/221 | 606/167 |
| 8,308,638 B2 * | 11/2012 | Hart | A61B 1/32 | 600/206 |
| 8,500,762 B2 * | 8/2013 | Sholev | A61B 17/00234 | 606/139 |
| 8,517,931 B2 * | 8/2013 | Minnelli | A61B 17/0218 | 600/201 |
| 8,574,627 B2 * | 11/2013 | Martakos | A61L 31/08 | 424/484 |
| 8,721,519 B2 * | 5/2014 | Sheu | A61F 2/0045 | 600/30 |
| 8,758,235 B2 * | 6/2014 | Jaworek | A61B 17/00234 | 600/206 |
| 8,764,646 B2 * | 7/2014 | Grundeman | A61B 17/02 | 600/207 |
| 8,814,788 B2 * | 8/2014 | Gan | A61B 17/0218 | 600/206 |
| 9,060,836 B2 * | 6/2015 | Jagger | A61F 2/0045 | |
| 9,220,597 B2 * | 12/2015 | Engstrand | A61F 2/28 | |
| 2002/0045800 A1 * | 4/2002 | Lau | A61F 2/2481 | 600/37 |
| 2002/0161391 A1 * | 10/2002 | Murphy | A61B 17/12109 | 606/200 |
| 2005/0203344 A1 * | 9/2005 | Orban | A61B 17/0218 | 600/204 |
| 2005/0245960 A1 * | 11/2005 | Grundeman | A61B 17/02 | 606/192 |
| 2006/0052669 A1 * | 3/2006 | Hart | A61B 1/32 | 600/206 |
| 2007/0208373 A1 * | 9/2007 | Zaver | A61F 2/01 | 606/200 |
| 2007/0265710 A1 * | 11/2007 | Brown | A61F 2/0063 | 623/23.72 |
| 2008/0097472 A1 * | 4/2008 | Agmon | A61B 17/42 | 606/119 |
| 2008/0118550 A1 * | 5/2008 | Martakos | A61L 31/14 | 424/445 |
| 2008/0146881 A1 * | 6/2008 | Alimi | A61B 17/02 | 600/204 |
| 2008/0178747 A1 * | 7/2008 | Baker | A47J 37/01 | 99/422 |
| 2008/0183044 A1 * | 7/2008 | Colleran | A61B 17/02 | 600/208 |
| 2009/0024147 A1 * | 1/2009 | Ralph | A61B 17/8028 | 606/151 |
| 2009/0062618 A1 * | 3/2009 | Drew | A61B 17/0218 | 600/204 |
| 2009/0137877 A1 * | 5/2009 | Minnelli | A61B 17/0218 | 600/204 |
| 2009/0137984 A1 * | 5/2009 | Minnelli | A61B 17/0218 | 604/540 |
| 2009/0198107 A1 * | 8/2009 | Park | A61B 17/02 | 600/215 |
| 2009/0216338 A1 * | 8/2009 | Gingras | A61F 2/0077 | 623/23.72 |
| 2009/0227844 A1 * | 9/2009 | Hart | A61B 1/32 | 600/208 |
| 2009/0287060 A1 * | 11/2009 | Pell | A61B 17/02 | 600/201 |
| 2010/0087713 A1 * | 4/2010 | Eliash | A61B 17/02 | 600/206 |

(56) References Cited

U.S. PATENT DOCUMENTS

| | | | |
|---|---|---|---|
| 2010/0114032 A1* | 5/2010 | Widenhouse | A61B 17/3421 604/167.03 |
| 2010/0174150 A1* | 7/2010 | Park | A61B 17/0218 600/218 |
| 2010/0249519 A1* | 9/2010 | Park | A61B 17/0218 600/206 |
| 2010/0292718 A1* | 11/2010 | Sholev | A61B 17/00234 606/151 |
| 2011/0040152 A1* | 2/2011 | Kim | A61B 17/0218 600/206 |
| 2011/0105848 A1 | 5/2011 | Sadovsky et al. | |
| 2011/0118706 A1* | 5/2011 | Gingras | A61B 17/00234 606/1 |
| 2011/0172495 A1* | 7/2011 | Armstrong | A61B 17/0218 600/233 |
| 2012/0046667 A1 | 2/2012 | Cherry et al. | |
| 2012/0238824 A1* | 9/2012 | Widenhouse | A61B 17/1155 600/207 |
| 2012/0289785 A1* | 11/2012 | Albrecht | A61B 17/0293 600/208 |
| 2013/0018228 A1* | 1/2013 | Armstrong | A61B 17/0218 600/204 |
| 2013/0018229 A1* | 1/2013 | Jaworek | A61B 17/00234 600/206 |
| 2013/0030253 A1* | 1/2013 | Titus | A61B 17/0281 600/207 |
| 2013/0066155 A1* | 3/2013 | Keating | A61B 17/0218 600/204 |
| 2013/0085339 A1* | 4/2013 | Jaworek | A61B 17/0218 600/204 |
| 2013/0109924 A1* | 5/2013 | Gan | A61B 17/0218 600/205 |
| 2013/0277613 A1* | 10/2013 | Miyagawa | C04B 35/64 252/301.4 R |
| 2014/0051915 A1* | 2/2014 | Sholev | A61B 17/00234 600/37 |
| 2014/0194698 A1* | 7/2014 | Melsheimer | A61B 17/0218 600/233 |
| 2014/0200409 A1* | 7/2014 | Green | A61B 1/32 600/208 |
| 2014/0296649 A1* | 10/2014 | Fehling | A61B 17/0293 600/208 |
| 2014/0364892 A1* | 12/2014 | Okoniewski | A61M 29/00 606/191 |
| 2015/0065805 A1* | 3/2015 | Edmondson | A61B 17/0218 600/204 |
| 2015/0150549 A1* | 6/2015 | Hirszowicz | A61F 2/02 433/173 |

* cited by examiner

ABDOMINAL RETRACTOR

CROSS-REFERENCE TO RELATED APPLICATIONS

This application claims the benefit of U.S. Provisional Application No. 61/750,395, filed Jan. 9, 2013, which is hereby incorporated by reference in its entirety.

FIELD OF THE INVENTION

The present disclosure pertains generally to retractors.

BACKGROUND

One of the greatest technical challenges during hand-assisted laparoscopic surgery such as sigmoid colectomy or ileo-colic resection is retracting loops of small bowel which drop repeatedly into the surgical field and obscure visualization. The lack of structural integrity of the bowels and organs allows them to impinge upon the workspace and interfere with the work of the surgeon. The usual method to prevent this interference is positioning the operating table into steep Trendelenburg position so as to allow gravity to assist in favorably shifting the viscera in a superior direction, but this can labor breathing and adversely affect circulation not to mention risk patient injury and positional hypotension.

Conventional retractors are sometimes used to retract bowels and organs from the workspace, but the slipperiness of the tissue can be a nuisance and can contribute to loss of retraction at crucial times. So, devices to prevent prolapse of small bowel loops into the operative field during laparoscopic or open abdomino-pelvic surgery have been developed. For example, small bowel is known to be packed proximally in the abdomen using laparotomy pads or towels. Laparotomy pads or towels inadvertently left inside the abdomen, however, pose the risk of surgical complication with serious consequences. Other methods of retracting the small bowel into the upper abdomen utilize a plastic bag, into which the small bowel is placed and usually secured by means of a pull-cord around the opening of the bag. This approach does not provide retraction of the small bowel out of the pelvis and additionally risks strangulation of the bowel itself from constriction of the mesenteric blood supply.

Some devices have tried to solve these issues by providing a frame with a membrane attached thereto. For example, US 2011/0172495 to Armstrong describes a biocompatible deformable retractor that comprises a deformable resilient frame and a deformable membrane attached to the frame. The retractor can be deployed inside the body cavity by deforming the retractor, inserting the deformed retractor into the body cavity through a surgical opening, and releasing the retractor in the body cavity to retract the organ in the cavity to form the working space. In Armstrong, the membrane can be constructed from a biocompatible sheet, fabric, net, or a combination thereof. Armstrong also discusses that, in some embodiments, it may be desirable to have perforation on the membrane for the purpose of passing surgical instruments such as a laparoscope through the membrane or that the membrane can alternatively be constructed from material that can be punctured by medical instruments. However, new retracting devices are desired.

SUMMARY

In some aspects, the present disclosure describes surgical retractors arranged to retract bowels and organs within the abdominal cavity of a patient. In accordance with some embodiments, a surgical retractor is configured to permit access to a select portion of bowel or organ being retracted without compromising the structural integrity of the surgical retractor. In some arrangements, the present disclosure teaches a surgical retractor comprising a frame defining a central opening; and a supporting structure extending across at least a portion of the central opening and comprising a series of intersecting strands defining strand openings there between; wherein the strand openings are enlargeable by slidable passage of the strands relative to one another. In some instances, the frame is deformably resilient. Alternatively or additionally, the intersecting strands can be interwoven and/or the strands of the supporting structure can be movable with respect to one another so as to change the arrangement of the strand openings.

In some embodiments, the surgical retractor comprises a frame defining a central opening; and a supporting structure extending across the central opening and comprising a web member defining web openings; wherein the frame extends through a plurality of the web openings. Alternatively or additionally, the frame can be deformably resilient and/or can be woven through a plurality of the web openings.

The present disclosure also teaches a surgical retractor comprising a frame defining a central opening; and a web member extending across at least a portion of the central opening and defining a plurality of web openings; wherein the web member comprises a monolithic polymeric structure defining a plurality of intersecting struts forming the web member. In some instances, the frame is deformably resilient and/or is woven through a plurality of the web openings. Additionally or alternatively, the web member can comprise web openings having a maximum dimension of less than approximately 1 inch. In some embodiments, the web member is free of knots and/or is flexibly resilient.

Further forms, objects, features, aspects, benefits, advantages, and embodiments of the present invention will become apparent from a detailed description and drawings provided herewith.

DESCRIPTION OF THE ILLUSTRATED EMBODIMENTS

Figure 1:
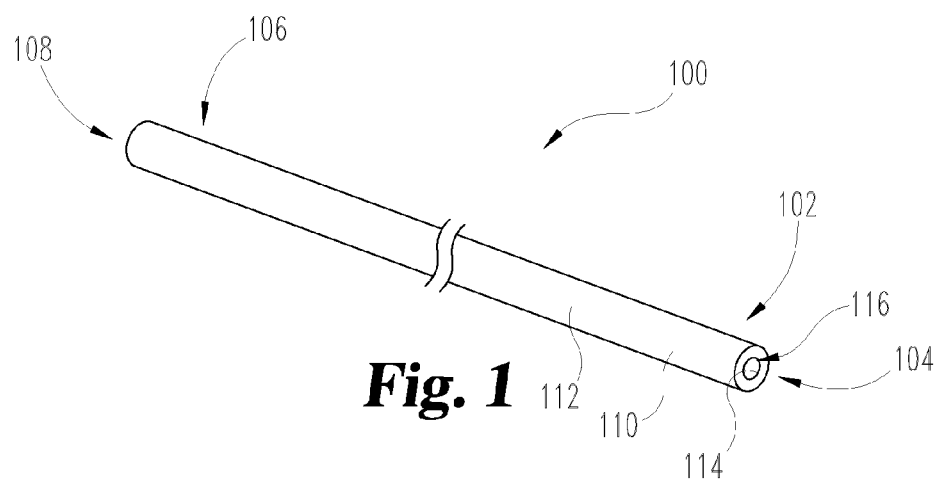
FIG. 1 is a perspective view of a frame in an elongate configuration.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The present disclosure pertains generally to retractors for retracting tissue of the body. For example, embodiments of the present disclosure may be used to retract organs in the abdomen of a patient so as to create a cavity that provides working space during surgery, such as laparoscopic procedures. In some aspects, the device can comprise of a frame defining a central opening and a supporting structure extending across at least a portion of the central opening.

The frame may form any of a variety of shapes. For example, the frame can have a bias and/or a memory so as to form a selected arrangement. In some instances, the frame can form an open or closed shape, such as a shape resembling a letter of the English alphabet such as C, O, S, or U, just to name a few non-limiting examples. In some embodiments, the frame is biased so as to form an open ovoid shape. In some embodiments, the frame forms a bean shape.

In some instances, the frame can comprise an elongated member having a first end region and a second end region, with the elongated member configurable between an elongate configuration and a loop configuration. In some instances, a first end region and a second end region of the elongated member are adjacent to one another in the loop configuration. Additionally, the first end region and the second end region may be coupled to one another and/or in abutting contact in the loop configuration so as to form a closed-loop arrangement. For example, the first and second ends can be connected by solvent-bonding and/or have portions arranged to mateably connect with one another, just to name a few non-limiting examples.

The cross-section of the frame can be any suitable shape. For example, in some instances, an extruded elongated frame member can have an ovoid cross-section. Alternatively, or additionally, the frame may have a cross section that is round, semi-circular, triangular, or polygonal in shape. In some instances, the frame has a cross-section that biases the frame into one or multiple configurations, such as an oblong or irregular cross-section. For example, in situations in which the frame is bent into a closed-loop configuration that defines a central opening, a rectangular cross-section will bias the frame so that one side of the frame faces towards the central opening and another side faces away. Advantageously, the frame could be rotated so that frame is biased into a position that faces a different side of the rectangular cross-section towards or away from the central opening.

In some embodiments, the frame can have one or more surfaces arranged to contact tissue. For example, the frame may have a surface with one or more protrusions, such as teeth or ridges to name a few non-limiting examples, arranged to contact tissue and resist movement of the frame relative to the tissue.

The frame can be fashioned from any suitable material, as will be apparent to one of ordinary skill in the art. In some embodiments the frame comprises a deformable resilient material so that the frame is deformably resilient. For example, in some instances the frame can comprise an elastomeric polymer. In some embodiments, the elastomeric polymer is extruded into an elongated body and can be configured into a loop configuration as described above. In some instances, it may be preferred to form the frame from one or more biocompatible materials, including, for example, metals, such as stainless steel or alloys, e.g., Nitinol®, or polymers such as polyether-amide block co-polymer (PEBAX®), nylon (polyamides), polyolefins, polyesters, polycarbonates or other suitable biocompatible polymers including elastomeric polymer, such as suitable polyurethanes, polydimethyl siloxane, acrylonitrile butadiene styrene (ABS), high density polyethylene (HDPE), rubber, polyisoprene (i.e., synthetic rubbers), and polytetrafluoroethylene. Spring metals or shape memory metals, such as Nitinol®, can be particularly useful. In some instances, the frame can be covered in a polymeric cover or the like. In some embodiments, different portions of frame can be formed from different materials to introduce desired stiffness/flexibility for the particular portion of the frame. In some embodiments, the frame can be made from polymer embedded with metal wire. Suitable polymers include, for example, polyamides, i.e., nylons. The metal wire can be braided, coiled or otherwise placed over a polymer tubing liner with some tension. A polymer jacket can be then placed over the top of metal wire or the like. Upon heating over the softening temperature of the polymer and subsequently cooling the polymer, the wire becomes embedded within the polymer. The liner and jacket can be the same or different materials. The wire adds additional mechanical strength while maintaining appropriate amounts of flexibility. In general, the frame is made of material that has sufficient resilience to substantially regain its resting configuration after being deformed, which is self-extendable. The frame may be a durometer from about 40 A to about 90 A on the A durometer scale or from about 50 D to about 90 D on the D durometer scale, as specified in ASTM protocol D2240-00. Frames formed from elastic polymers, such as rubbers or the like, can be convenient and relatively inexpensive.

In some embodiments, the frame provides support for the supporting structure. For example, the frame can extend and/or spread the supporting structure in one or more directions. Alternatively, or additionally, the frame may apply tension to the supporting structure so as to limit the deformation and/or resistance to deformation of the supporting structure.

In some instances, the supporting structure extends across at least a portion of the central opening. In some embodiments, the frame encircles the supporting structure. Alternatively, or additionally, portions of the supporting structure may extend from within the central opening to a location beyond the frame, such as a location outside of the central opening and not encircled by the frame. For example, portions of the supporting structure may extend beyond the perimeter of the frame and define loops. Such loops may be arranged to contact tissue within the body of the patient so as to resist movement of the frame and/or supporting structure relative to the tissue. Alternatively or additionally, such loops may be arranged to receive a suture so that the surgical retractor may be temporarily retained in position within the body of the patient during a surgical procedure. As will be appreciated by one of ordinary skill in the art, portions or the supporting structure and/or frame may also be arranged for association with other medical devices. For example, portions can be arranged to retain and or support a surgical tool such as a suction device and/or a clamp, just to name a few non-limiting examples.

In some embodiments, the supporting structure comprises a plurality of strands. For example, the supporting structure can comprise a plurality of polymeric strands that extend across the central opening and are coupled to the frame at each end. In some instances, the strands define strand openings there between.

In some instances, the supporting structure comprises a series of intersecting strands. For example, one or more strands may extend along a first direction across the central opening with one or more other strands extending along a second direction across the central opening, wherein the first and second directions are transverse to one another and the strands intersect within the central opening. In some embodiments, the supporting structure comprises a first plurality of parallel strands and a second plurality of parallel strands, wherein the first plurality of parallel strands extends in a direction transverse to the direction in which the second plurality of parallel strands extend. In some instances, the intersecting strands extend in directions substantially orthogonal to one another. As will be discussed in more detail below, the strands may be deflectable and/or movable relative to one another. For example, the parallel and/or transverse strands may be slidable along one another.

In some arrangements, it may be preferred that strands of the supporting structure are interwoven. For example, portions of the supporting structure may have interwoven strands to change the structural characteristics of the supporting structure. In some instances, weaving strands of the supporting structure changes the resilience of the supporting structure and/or the resistance to deformation or movement of the supporting structure and/or the strands relative to one another.

In some embodiments, the supporting structure comprises multiple layers of strands. For example, the supporting structure may have one or more layers of strands extending along a first direction and another layer of strands extending along a second direction that is transverse to the first direction. Alternatively or additionally, one or more strands from a layer of strands may be interwoven with one or more strands from another layer.

In some embodiments, the strands are deflectable and/or movable with respect to one another. This can allow the creation, enlargement, and/or alteration of the shape of an opening defined by the strands without compromising the integrity of the supporting structure due to the cutting or puncture of a portion of the supporting structure. For example, in some instances, a first strand may individually define an eyelet arranged for receiving a second strand. This can allow the first strand to be cut and/or severed at a location remote from the eyelet but yet maintain coupling of the first and second strands. In other words, a portion of the supporting structure, such as a strand, can be cut without completely collapsing a strand. In some instances, including those with and without eyelets, the supporting structure comprises movable warp and weft. For example, the strand openings defined by the strands (e.g., the warp and weft) can be enlargeable by slidable passage of the strands relative to one another.

In some instances, the strands are configurable to change the arrangement of an opening, such as the size, shape, and/or the location of the opening. For example, in some embodiments, the strands are slidable with respect to one another, and slidable passage of the strands relative to one another enlarges an opening and shrinks or eliminates another opening, such as an adjacent one. In some instances, the strands are capable of returning to an undeflected configuration to close the opening or return the opening to an initial configuration (e.g., such as an initial size and/or shape).

As will be appreciated by one of ordinary skill in the art, the strands may have any of a number of shapes. For instance, the strands may comprise a ribbon shape having a polygonal cross section. Alternatively, or additionally, the strands may have a cylindrical shape having a circular cross section.

In some instances, the shape of the strand varies along a length of the strand. For example, a first and/or a second end region of a strand may have a first shape and a central region of the strand having a second shape. As will be appreciated, the shape of the strands can be arranged so as to achieve a desired traction between the abdominal retractor and adjacent tissue and/or to achieve a desired relationship between strands of the supporting structure. For example, an end of a strand can have a ribbon shape with the central region of the strand having a cylindrical shape or vice versa.

In some instances, an abdominal retractor can have strands with ribbon portions around the frame that provide sufficient traction between the abdominal retractor and adjacent tissue so as to resist undesired movement of the abdominal retractor during surgery but with a profile smaller than that of larger cross-sectional strands. Advantageously, this can reduce the trauma to the tissue. Additionally or alternatively, arrangements having strands with ribbon portions in the central region can increase the frictional resistance between contacting strands so as to resist sliding movement of one strand relative to another. This can advantageously improve the resistance to bowel extending into and enlarging the openings defined by the strands and extending into the operating space.

In some embodiments, the strands can comprise an elongated body having a first end and a second end. However, in some instances, the strands may have multiple elongated portions and/or more than two ends. For example, in some embodiments, the strands can comprise a Y shape with the ends of each strut of the Y coupled to the frame.

In some instances, the supporting structure comprises a web member comprising a plurality of struts defining web openings there between. For example, the web member may comprise a monolithic polymeric structure defining a plurality of intersecting struts forming the web member. In some instances the struts are integrally formed in the web member so that the web member is free of knots, seams, or joints at the intersections of the struts.

As will be appreciated by one of ordinary skill in the art, the supporting structure can comprise any suitable material, such as an elastomeric material. For example, the strands and/or struts may comprise biocompatible materials, including, for example, polymers such as polyether-amide block co-polymer (PEBAX®), nylon (polyamides), polyolefins, polyesters, polycarbonates or other suitable biocompatible polymers including elastomeric polymer, such as suitable polyurethanes, polydimethyl siloxane, acrylonitrile butadiene styrene (ABS), high density polyethylene (HDPE), rubber, polyisoprene (i.e., synthetic rubbers), and polytetrafluoroethylene. In some embodiments, the supporting structure can be made from an elastomer such as polyisoprene, polyurethane, silicone polyurethane, or silicone. In some instances, the supporting structure may be non-elastic or only slightly elastic so that the supporting structure can restrain organs or other body portions without significantly distending the supporting structure. Thus, inelastic materials such as polyethylene terephthalate can be used to form the supporting structure or portions thereof. In some instances, the strands and/or struts of the supporting structure, such as a warp and weft, can be fashioned from identical or different materials.

In some instances, a first strand of the supporting structure can comprise a material that is cohesive to a material of a second strand. In some cases, these strands can be intentionally separated and/or attached so as to allow a user of the abdominal retractor to adjust the shape and/or size of the openings defined by the strands. For example, in some embodiments, a first strand and a second strand can comprise a hook and loop type fastener, such as one of the hook and loop fasteners sold under the trademark Velcro®, with the hook material positioned on the first strand and the loop material positioned on the second strand. When the two strands are brought into contact, the hook material engages the loop material and detachably couples the first and second strands to one another.

In some embodiments, a surface of the abdominal retractor is arranged for a desired resistance to relative movement. For example, the surface of the supporting structure can be arranged to resist movement between the strands and/or struts of the supporting structure and adjacent tissue, the frame, and/or other strands and/or struts. For example, a portion of a surface of a strand can have a surface texture arranged to resist the strand from sliding along and/or around the frame. This can be achieved by arranging the lay, surface roughness, and/or the waviness of the surface. In some instances, the surface of the abdominal retractor has an average surface roughness ($R_a$) of less than about $5 \times 10^{-4}$ inches. However, the surface may have an average roughness greater than $1 \times 10^{-3}$ inches or, in some instances, greater than $1 \times 10^{-2}$ inches.

The strands and/or struts may have a maximum cross-sectional dimension (e.g., width) from about 1/64 of an inch to about 1 inch and in some embodiments of about 1/32 of an inch to about 1/8 of an inch. A person of ordinary skill in the art will recognize that additional ranges of thickness within the explicit ranges above are contemplated and are within the present disclosure.

The size, shape, and configuration of the openings in the supporting structure may vary, as will be appreciated by one of ordinary skill in the art. For example, in some embodiments, the openings can have a circular or polygonal shape. Additionally, or alternatively, a plurality of openings in the supporting structure may be arranged in columns and/or rows and/or may be arranged to form a shape, such as a circular or semi-circular or polygonal configuration. In some instances, the openings have a maximum dimension of less than approximately 1 inch in width. Preferably, the openings have a maximum dimension of less than ½ of an inch. More preferably, the openings have a maximum dimension of about 5/32 of an inch to about 15/16 of an inch.

The supporting structure can be coupled to the frame in any suitable manner, as will be apparent to one of ordinary skill in the art. For example, the supporting structure can be coupled to the frame along a portion of the perimeter of the supporting structure. Alternatively, or additionally, inner portions of the supporting structure may be coupled to the frame, with outer portions of the supporting structure, such as a perimeter portion, cateleveredly supported by and/or coupled to the frame.

In some instances, portions of the supporting structure can be adhered to the frame using an adhesive. Alternatively, or additionally, portions of the supporting structure can be coupled to the frame using a coupling member, such as a tie strap or a clip, to name a few non-limiting examples. In some embodiments, the supporting structure and frame are coupled to one another during the formation of the supporting structure and/or the frame. For example, the supporting structure may be molded around the frame. Alternatively, portions of the frame may be molded around portions of the supporting structure.

In some instances, an end region of a strand of the supporting structure extends around a portion of the frame and is attached to a central region of the strand. As will be appreciated, the strand can be attached to itself by any means apparent to one of skill in the art. For example, the strand may be stitched, adhered, and/or heat bonded to itself.

In some embodiments, the supporting structure and the frame are coupled to one another by extending the frame through openings in the supporting structure, such as strand openings or web openings. For example, the frame may extend through a plurality of web openings defined by struts of a web member along a perimeter portion of the supporting structure. Advantageously, this arrangement can reduce and/or eliminate the need to fold the supporting structure over the frame and couple the supporting structure to itself, such as by stitching or heat bonding.

In some instances, the frame is woven through openings defined by portions of the supporting structure. For example, the frame may be interwoven through a plurality of web openings defined by struts of web member along a perimeter portion of the supporting structure. Advantageously, weaving the frame through portions of the supporting structure can position adjacent portions of the supporting structure on alternating sides of the frame so as to couple the frame and the supporting structure to one another without the use of adhesives or coupling members. Weaving the frame through openings in the supporting structure can also aid in positioning the supporting structure between the top and bottom surfaces of the frame within the central opening. For example, if the supporting structure comprises a web member comprising a plurality of struts with adjacent struts contacting different sides of the frame (e.g., the top side or the bottom side) the central portion of the web member will be located substantially medial the top and bottom surfaces of the frame.

As will be appreciated by one of ordinary skill in the art, the supporting structure can be fashioned as a molded or woven web that may be flexible yet pulled taut by the bias of the perimeter frame. The warp and weft of the web member can be attached to the perimeter frame and/or can be attached to one another, and an opening defined by the stands and/or struts of the web member can be enlarged by cutting or shifting the warp and weft to selectively form a window in the web member.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates an elongated member 100 having a first end region 102 and a second end region 106. First end region 102 has a first end 104 and second end region 106 has a second end 108. In some instances, elongated member 100 comprises a tube having a tube wall 110 with an outer surface 112 and an inner surface 114 that defines an inner lumen 116.

Figure 2:
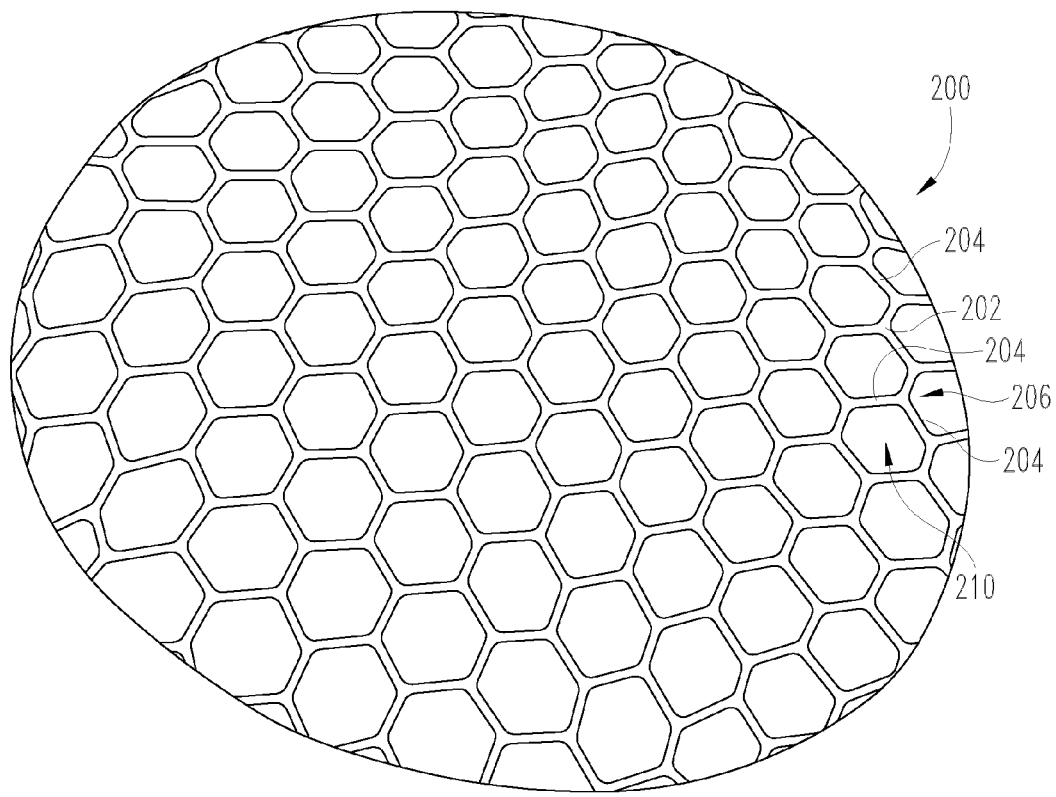
FIG. 2 is a perspective view of a supporting structure.

FIG. 2 illustrates a supporting structure 200 of some embodiments of a retractor. Supporting structure 200 comprises a web member 202 having struts 204 intersecting at intersections 206. Struts 204 are arranged to retain bowels and organs and define web openings 210 that allow for visualization of the bowels and organs through supporting structure 200. Additionally, web openings 210 can be arranged to allow medical instruments to pass through web member 202 without compromising the integrity of supporting structure 200.

Figure 3:
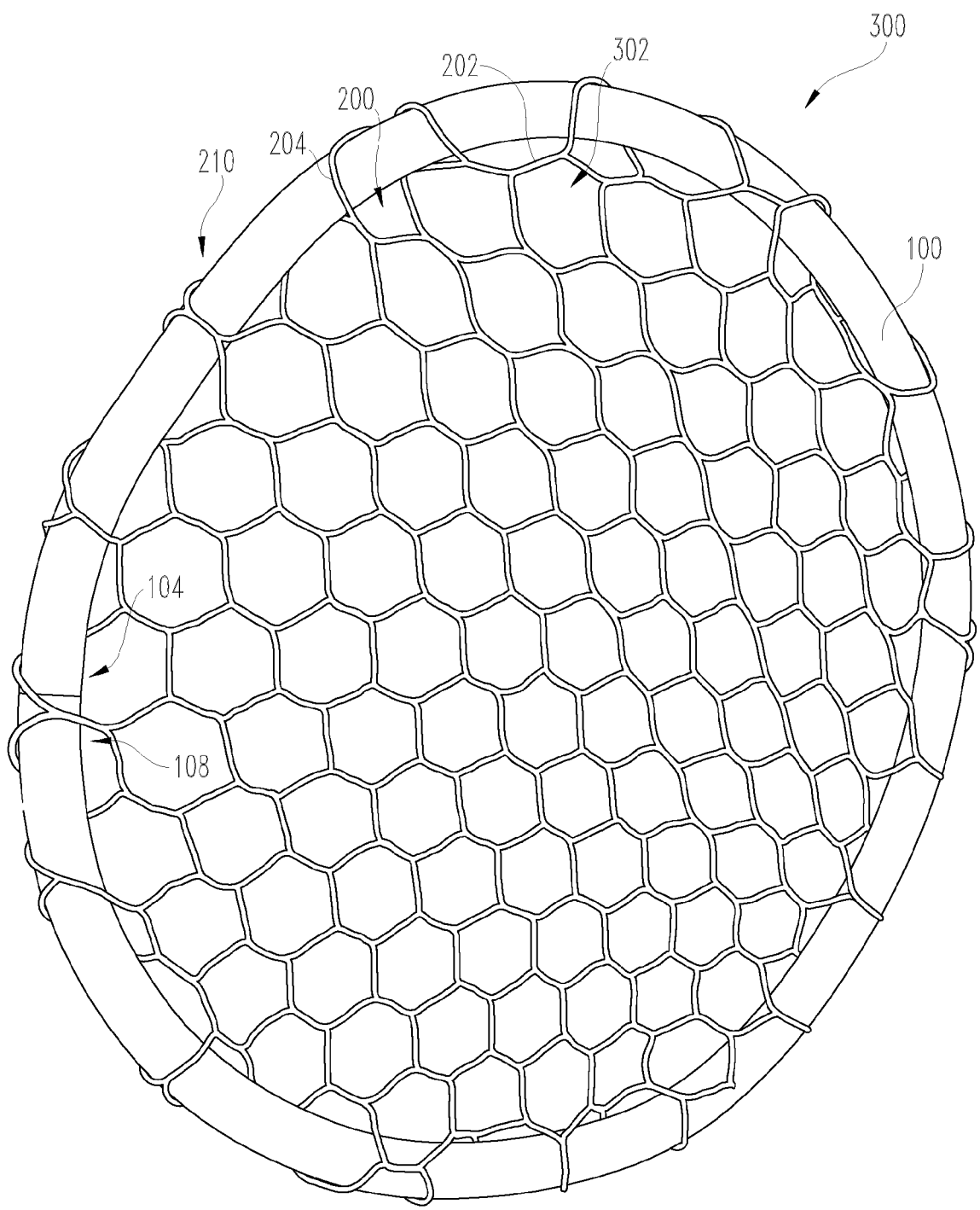
FIG. 3 is a top plan view of one embodiment of a surgical retractor.

FIG. 3 illustrates one embodiment of a retractor 300 having an elongated member 100 configured into a closed-loop configuration, wherein first end 104 and second end 108 are brought into close proximity with one another and are coupled to one another. For example, the first and second ends 104, 108 can be solvent-bonded to one another so as to secure elongated member 100 into a closed-loop configuration. When elongated member 100 is formed into the loop configuration illustrated in FIG. 3, retractor 300 defines a central opening 302. Supporting structure 200 can be positioned within central opening 302 and extend across at least a portion of the central opening 302 to connect different portions of elongated member 100.

Supporting structure 200 illustrated in FIG. 3 comprises a web member 202 having a monolithic-polymeric structure with web openings 210 positioned around a perimeter thereof and arranged to receive elongated member 100. In some embodiments, elongated member 100 can be interwoven through web openings 210 defined by supporting structure 200, as illustrated in FIG. 3. Interweaving elongated member 100 through supporting structure 200 can position adjacent struts 204 of supporting structure 200 on opposing sides of elongated member 100.

Figure 4:
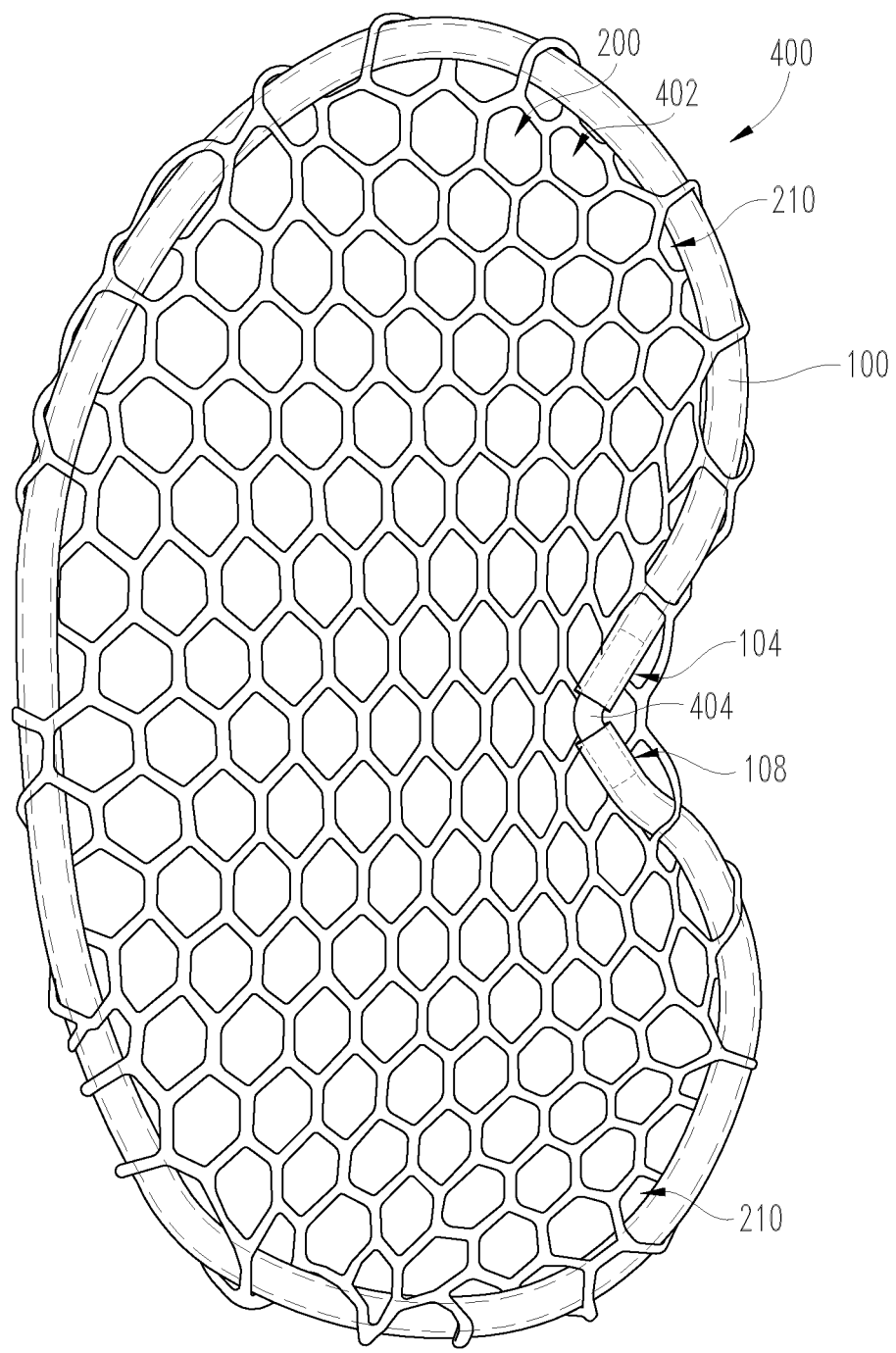
FIG. 4 is a top plan view of one embodiment of a surgical retractor.

FIG. 4 illustrates another embodiment of a retractor, comprising retractor 400 arranged into a bean-shaped configuration. Similar to the retractor 300 illustrated in FIG. 3, retractor 400 defines a central opening 402 for receiving a supporting structure 200. Elongated member 100 of retractor 400 is configured into a closed-loop configuration with first end 104 and second end 108 coupled to one another by an end connecting coupling member 404. Additionally or alternatively, elongated member 100 can be formed into a closed-loop configuration and/or bean shape by the selective weaving of elongated member 100 through web openings 210 in the supporting structure 200. For example, elongated member 100 may be woven through a plurality of web openings 210 positioned along a bean-shaped path so that struts 204 defining web openings 210 retain elongated member 100 in a bean shape.

Figure 5:
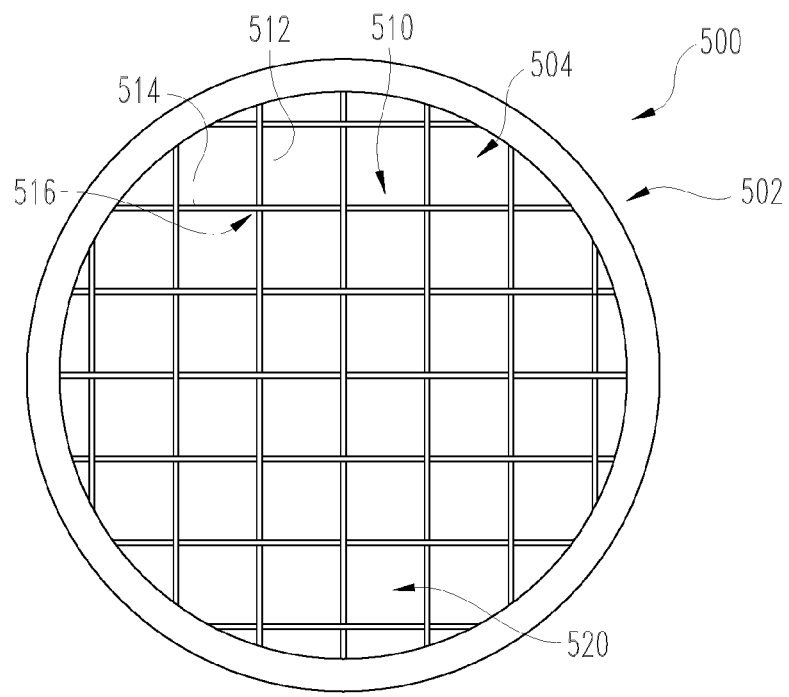
FIG. 5 is a top plan view of one embodiment of a surgical retractor.
Figure 6:
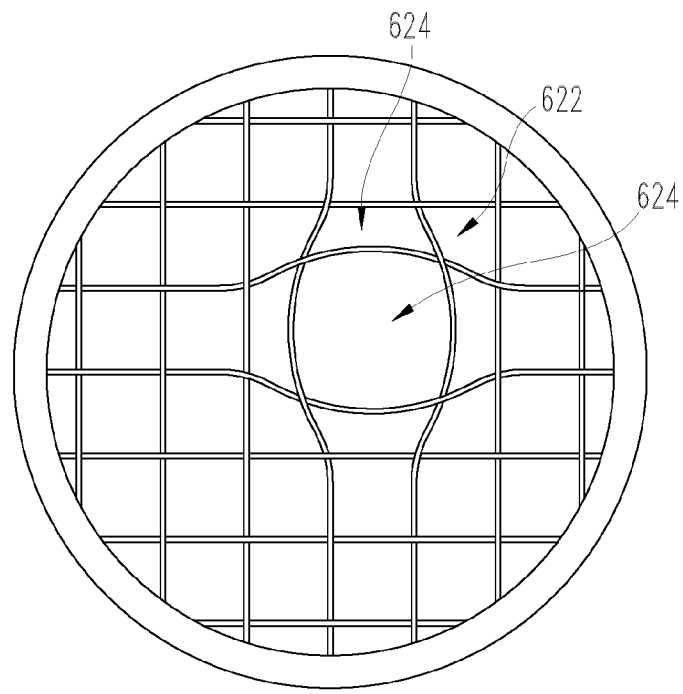
FIG. 6 is a top plan view of the embodiment of FIG. 5 with strands configured into an enlarged opening configuration.

FIGS. 5 and 6 illustrate a retractor 500 comprising a frame 502 defining a central opening 504. Positioned within central opening 504 is a supporting structure 510 that extends across at least a portion of central opening 504 and connects different portions of frame 502. As illustrated in FIG. 5, supporting structure 510 comprises a plurality of strands, such as vertical strands 512 and horizontal strands 514. Vertical strands 512 and horizontal strands 514 extend in transverse directions and intersect at intersections 516. In some embodiments, strands of supporting structure 510 extend substantially orthogonal to one another. In some instances, vertical strands 512 and horizontal strands 514 are woven such that intersections 516 along a length of a strand, such as vertical strand 512 and/or horizontal strand, alternate between a first intersecting strand being positioned on the top or the bottom of a second intersecting strand. Vertical strands 512 and horizontal strands 514 define strand openings 520 that are enlargeable.

As illustrated in FIG. 6, vertical strands 512 and horizontal strands 514 may be slidably passed relative to one another so as to enlarge one or more strand openings 520. In some instances, slidable passage of vertical strands 512 and/or horizontal strands 514 relative to one another enlarges one or more strand openings 520 into a larger strand opening 622 and correspondingly shrinks or eliminates adjacent strand openings 624.

Figure 7:
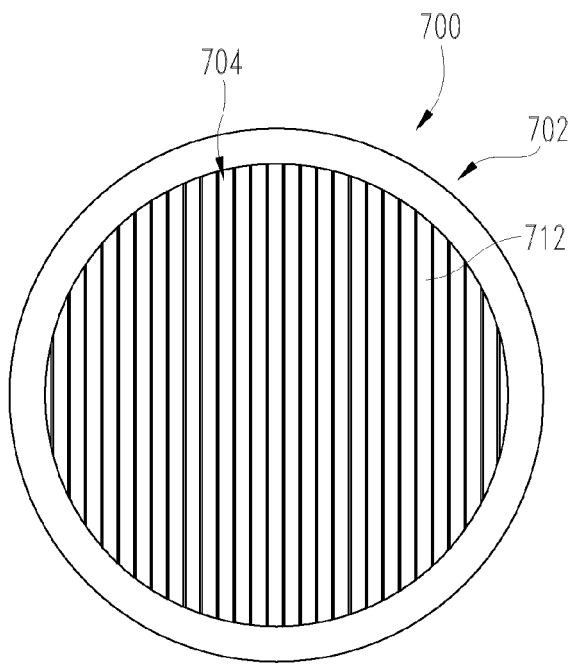
FIG. 7 is a top plan view of one embodiment of a surgical retractor.
Figure 8:
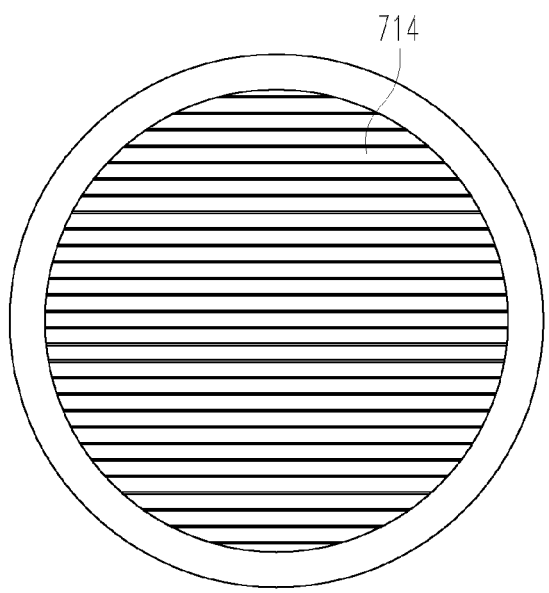
FIG. 8 is a bottom plan view of the bottom of the embodiment in FIG. 7.
Figure 9:
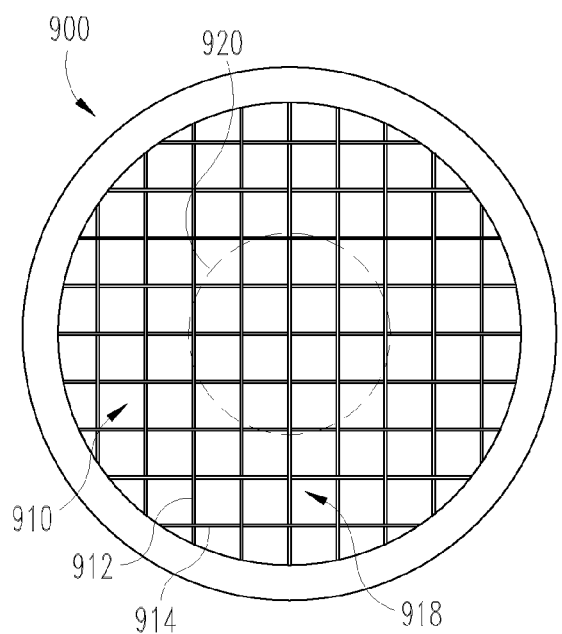
FIG. 9 is a top plan view of one embodiment of a surgical retractor.

In some embodiments, strands of the retractor can be layered and may or may not be woven with one another. As illustrated in FIGS. 7 and 8, a retractor 700 can have vertical strands 712 layered on top of horizontal strands 714. Viewed from a top plan view, vertical strands 712 extend across central opening 704 defined by frame 702 of retractor 700. In some instances, as illustrated in FIG. 7, two or more vertical strands 712 are in abutting contact with one another. When viewed from a bottom plan view, horizontal strands 714 extend across central opening 704 and provide a second layer of strands across central opening 704.

In some embodiments, the strands of the retractor may have both interwoven portions and non-interwoven portions. For example, retractor 900 comprises a supporting structure 910 having vertical strands 912 and horizontal strands 914 intersecting vertical strands 912. In interwoven portion 918 of supporting structure 910, vertical strands 912 and horizontal strands 914 are interwoven, e.g., they alternate position along a length of a strand 912, 914. In non-interwoven portion 920 of supporting structure 910, vertical strands 912 and horizontal strands 914 and are not interwoven, e.g., they remain on the same side of each other.

Figure 10:
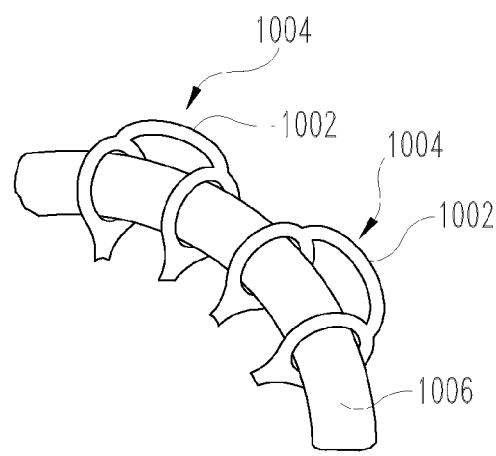
FIG. 10 is a perspective view of a portion of one embodiment of a surgical retractor and supporting structure.

FIG. 10 illustrates a portion of a retractor having strands 1002 defining loops 1004. As mentioned above, strands 1002 and loops 1004 can be a portion of the supporting structure that extends beyond the periphery of the frame 1006 and/or can be arranged to receive one or more sutures to retain portions of the retractor to adjacent tissue. For example, after the retractor is positioned within the abdominal cavity of a patient, a medical professional may suture loops 1004 to adjacent tissue so as to retain the retractor in position. Then, prior to removal of the retractor from the patient, the sutures may be cut or severed.

Figure 11:
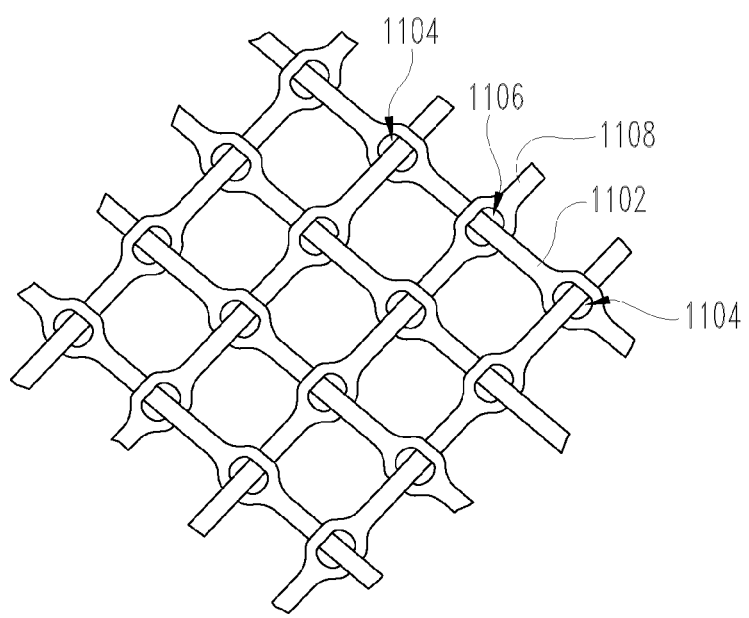
FIG. 11 is a top plan view of one embodiment of a supporting structure.

FIG. 11 illustrates a portion of a supporting structure comprising a strand 1102 that individually defines eyelets 1104 arranged to receive at least one other strand of the supporting structure. In some instances, a strand 1102 that defines an eyelet 1104 also passes through an eyelet 1106 defined by a separate strand 1108. Strands 1102, 1108 and/or eyelets 1104, 1106 can be arranged to allow for slidable passage of one strand relative to another. Similarly, strands 1102, 1108 and eyelets 1104, 1106 can allow for the selective severing of a strand without compromising the integrity of the supporting structure. For example, strand 1102 can be severed near eyelet 1106, illustrated in FIG. 11, but still support adjacent and/or crossing strands through eyelets 1104.

Figure 12:
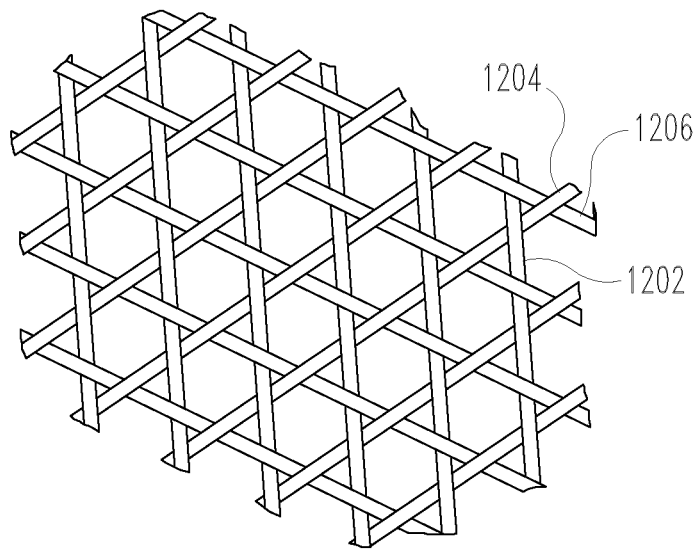
FIG. 12 is a top plan view of another embodiment of supporting structure.
Figure 13:
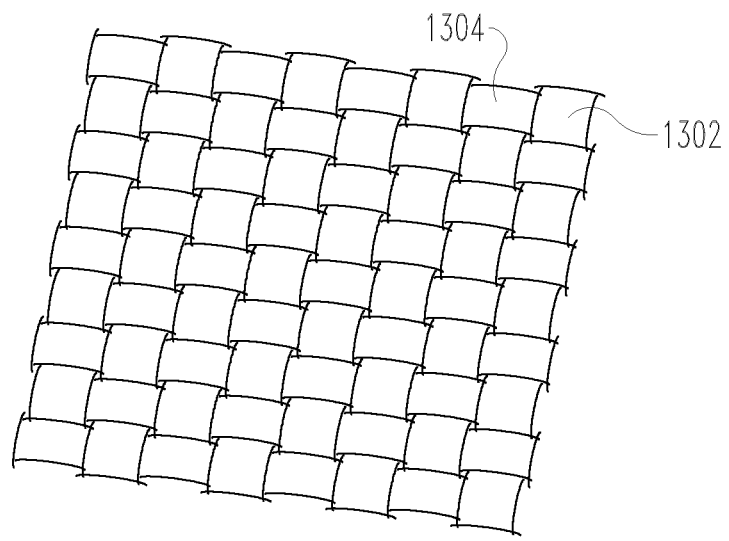
FIG. 13 is a top plan view of another embodiment of supporting structure.

FIGS. 12 and 13 illustrate additional embodiments of the supporting structure. As seen in FIG. 12, two or more strands, such as strands 1202, 1204, and 1206, can intersect at any number of angles. For example, strands 1202 and 1204 may intersect at substantially right angles or at oblique angles. As mentioned above, the supporting structure may comprise multiple layers of strands that can be interwoven with each other. As illustrated in FIG. 13, strands 1302 and/or 1304 may be have a length and width substantially greater than the thickness of the strand 1302 or 1304. In some instances, strands 1302 and/or 1304 are in the form of a ribbon.

Figure 14:
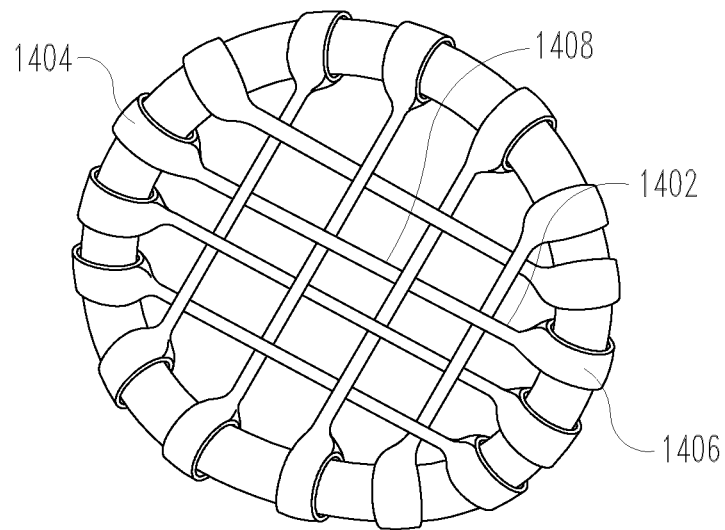
FIG. 14 is a top plan view of one embodiment of a surgical retractor.

FIG. 14 illustrates one embodiment in which the shape and/or size of a strand 1402 varies along the length of strand 1402. For example, ends 1404 and 1406 of strand 1402 can have a rectangular cross-section while central portion 1408 of strand 1402 can have a circular cross section. Similarly, ends 1404 and 1406 of strand 1402 can have a substantially larger or smaller maximum outer dimension than central portion 1408.

Figure 15:
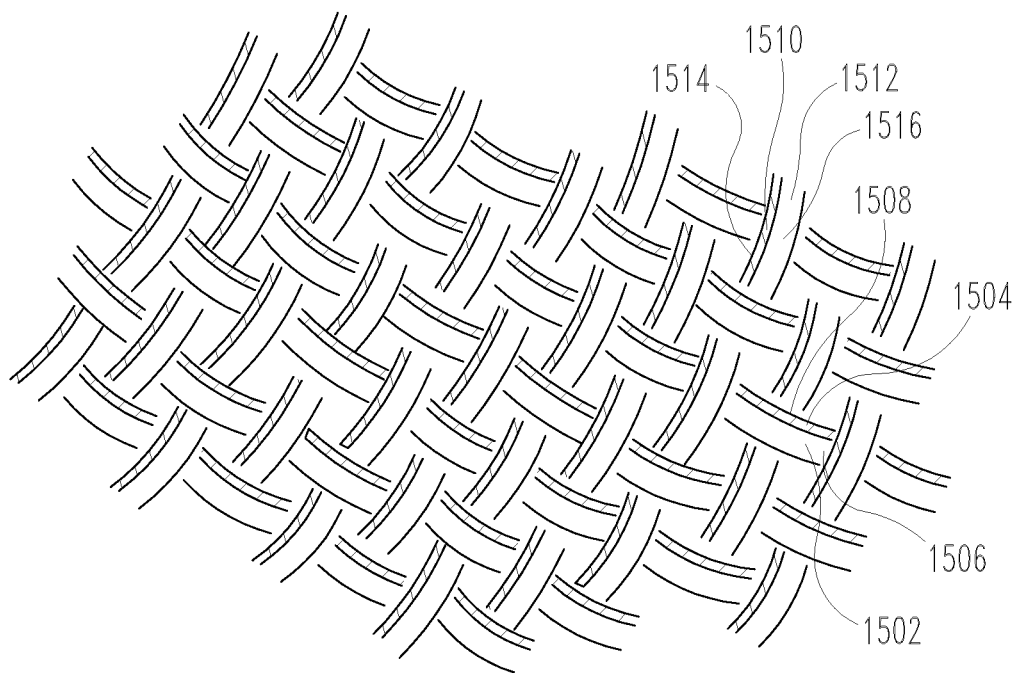
FIG. 15 is a top plan view of one embodiment of supporting structure.

FIG. 15 illustrates an embodiment in which the supporting structure comprises strands that are cohesive to one another. For example, a first strand 1502 can comprise a first surface 1504 and a second surface 1506, with first surface 1504 comprising a first cohesive member 1508, such as hooks. A second strand 1510 can comprise a third surface 1512 and a fourth surface 1514, with third surface 1512 facing first surface 1504 of first strand 1502 when first and second strands 1502 and 1510 are arranged to form a supporting structure and comprising a second cohesive member 1516, such as loops, arranged to cooperate with the first cohesive member 1508 of first strand 1502 to adhere first and second strands 1502 and 1510 together.

Figure 16:
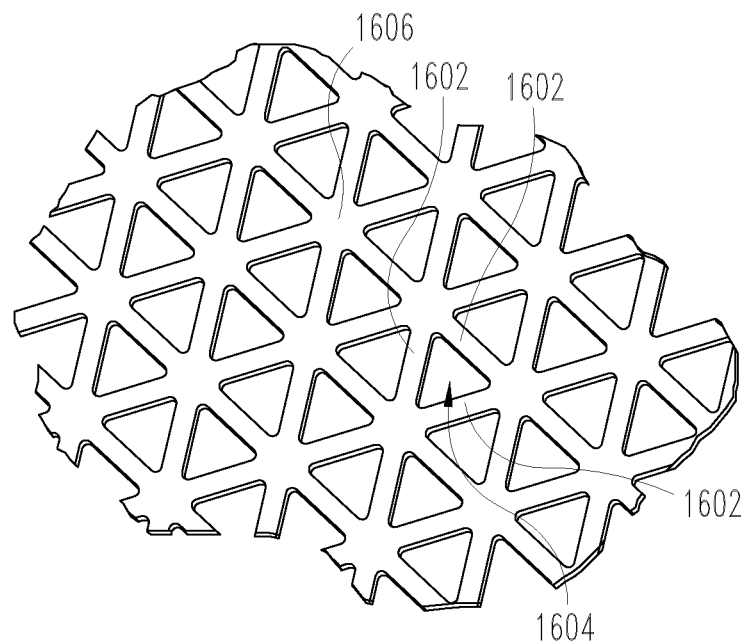
FIG. 16 is a top plan view of another embodiment of supporting structure.

FIG. 16 illustrates one embodiment of a supporting structure, such as a monolithic polymeric web material. As will be appreciated by one of skill in the art, the web material may have struts and openings of any number of shapes and sizes. For example, struts 1602 of the supporting structure illustrated in FIG. 16 define openings 1604. In some instances, openings 1604 are polygonal in shape, such as triangular; however, openings 1604 may be in a number of tessellating shapes. In some embodiments, struts 1602 are joined at one or more vertices 1606 and can be coupled in a number of ways such as being integrally molded, heat bonded, and/or adhered together, just to name a few non-limiting examples.

Figure 17:
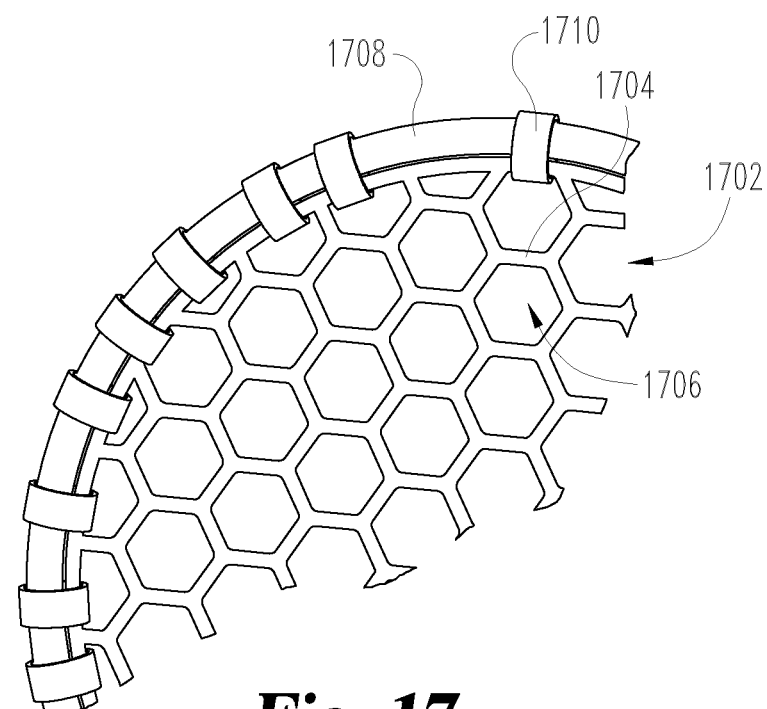
FIG. 17 is a top plan view of a portion of one embodiment of a surgical retractor.
Figure 18:
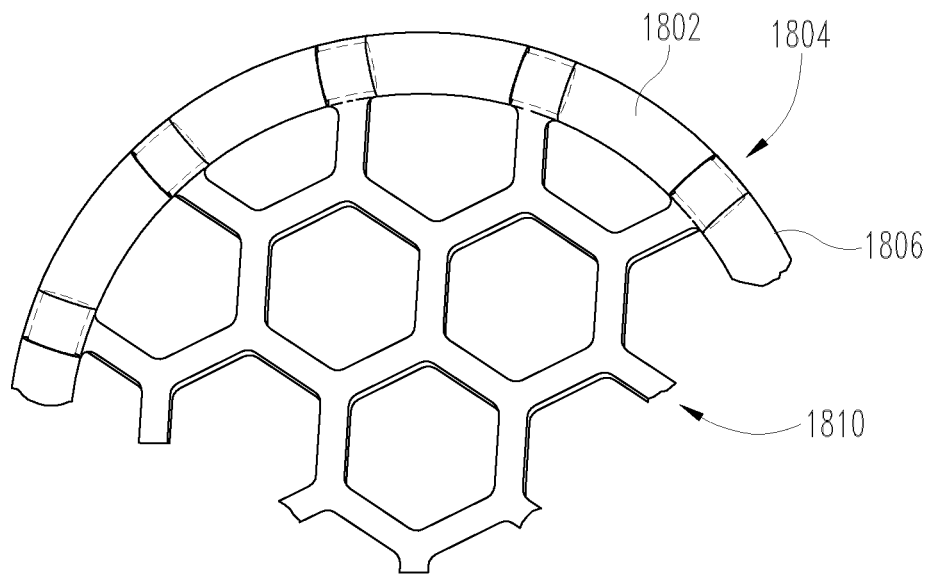
FIG. 18 is a top plan view of a portion of another embodiment of a surgical retractor.
Figure 19:
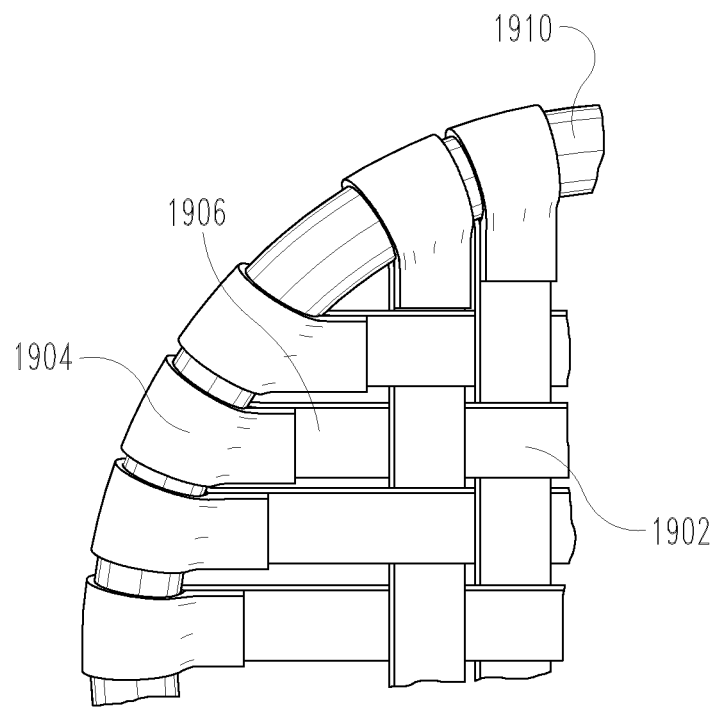
FIG. 19 is a top plan view of a portion of another embodiment of a surgical retractor.

FIGS. 17, 18, and 19 illustrate some embodiments of how the supporting structure can be coupled to the frame. In FIG. 17, the supporting structure 1702 comprises struts 1704 that define openings 1706. Frame 1708 extends along the periphery of supporting structure 1702 and is coupled to supporting structure 1702 by clips or bands 1710. In some instances, bands 1710 extend around frame 1708 and a strut 1704 of supporting structure 1702, such as by extending through an opening 1706.

In FIG. 18, frame 1802 comprises recessed portions 1804 in which outer surface 1806 of frame 1802 defines a notch or groove. Advantageously, portions of supporting structure 1810 and/or coupling members that couple supporting structure 1810 and frame 1802 can be positioned within recessed portions 1804 so as to produce a retractor with a substantially smooth outer perimeter, so as to reduce the trauma to tissue. Additionally or alternatively, positioning portions of supporting structure 1810 and/or the coupling members within the recessed portions 1804 can resist the sliding of those portions/members along the length of frame 1802. In some embodiments, supporting structure 1810 has portions molded around and substantially residing within recessed portions 1804.

FIG. 19 illustrates an embodiment of a retractor in which one or more strands 1902 comprise an end region 1904 and a central region 1906. To couple a strand 1902 to frame 1910, end region 1904 of strand 1902 is wrapped around frame 1910 and attached to central region 1906. In some instances, the strand can be attached to itself by stitches, adhesive, and/or heat bonding, just to name a few non-limiting examples.

Figure 20:
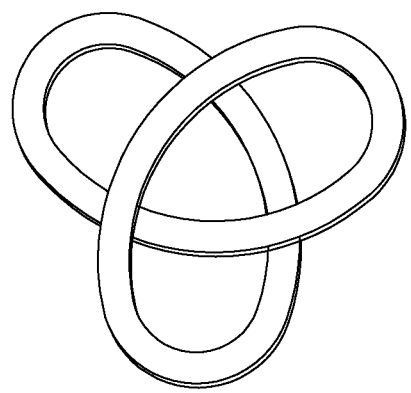
FIG. 20 is a top plan view of one embodiment of a frame in a folded configuration.

FIG. 20 illustrates a folded configuration of a frame and/or a retractor. For example, the retractor may be folded and/or bent into an insertable and/or packagable configuration. In some instances, a portion of the retractor is twisted 180° or a multiple thereof and then folded about the twisted portion of the retractor. Similarly, in some embodiments, the retractor can be folded similar to how a band saw blade is folded.

Figure 21:
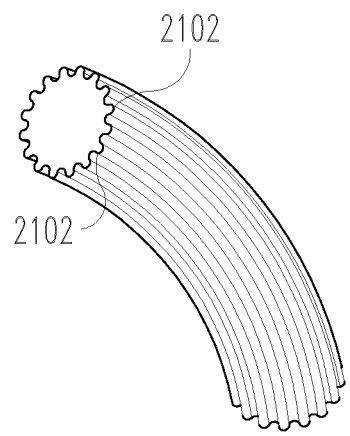
FIG. 21 is a perspective view of a section of one embodiment of a frame.

FIG. 21 illustrates a portion of a frame having protrusions along the outer surface of the frame. In some instances, protrusions extend along a length of the frame and form a plurality of ridges 2102 extending substantially parallel to one another. In other instances, the protrusions are discrete raised portions, such as bumps or knobs, that are positioned along a portion of the outer surface of the frame in a regular and/or irregular pattern.

Figure 22:
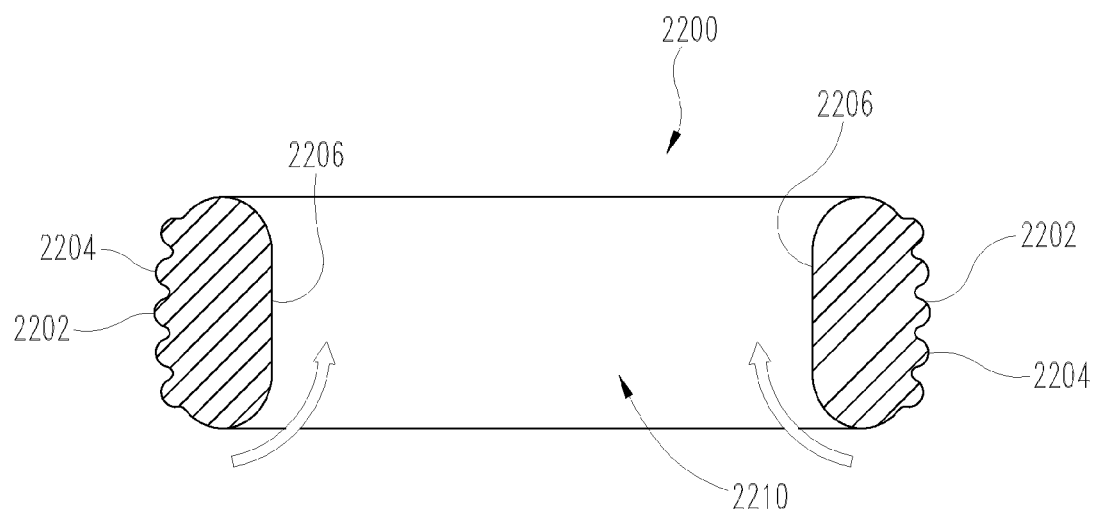
FIGS. 22 and 23 are cross-sectional views of a frame in biased configurations.
Figure 23:
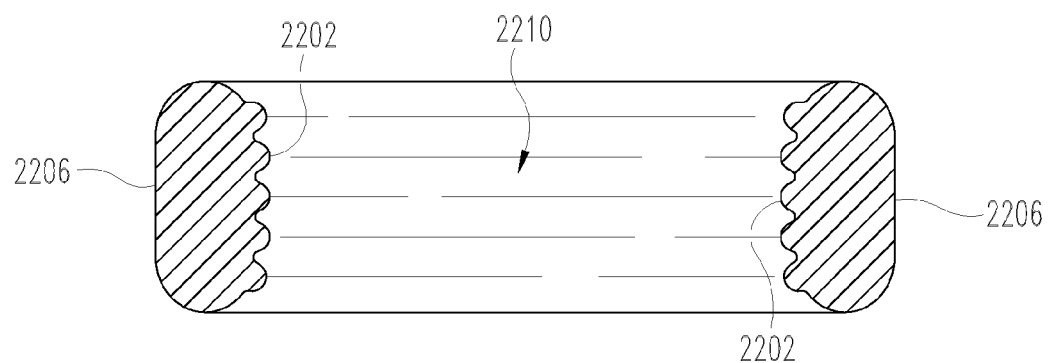

In some embodiments, the frame has some portions with protrusions and some portions free of protrusions. For example, as illustrated in FIGS. 22 and 23, the frame 2200 may have a first surface 2202 comprising protrusions 2204 and a second surface 2206 free of protrusions.

In some instances, the frame is configurable between one or more configurations. For example, in a first configuration, illustrated in FIG. 22, the frame 2200 may position first surface 2202 towards adjacent tissue and away from the central opening 2210 of frame 2200. Alternatively, the frame may be configurable, such as by rolling the frame around itself in the direction indicated by the arrows in FIG. 22, so as to position second surface 2206 away from the central opening 2210 and first surface 2202 towards central opening 2210, as illustrated in FIG. 23.

As will be appreciated, a frame can be arranged so that it is biased into one or more configurations. For example, constructing a closed-loop frame with an oblong cross-section can bias the frame into one of two configurations, such as those illustrated in FIGS. 22 and 23. As discussed above, the cross-section of the frame can have a number of shapes and can be arranged to be configurable into a number of biased and/or unbiased configurations.

It should be appreciated that frames are not limited to having merely two biased configurations. For example, frames having a polygonal cross section with three or more sides can be arranged so as to be configurable into three or more biased configurations. Advantageously, in embodiments in which the frame comprises surfaces having different characteristics (e.g., texture), the medical professional may configure the frame into a biased configuration in which the desired tissue-contacting surface faces towards the tissue of the patient.

The disclosed retractor embodiments can have frames that are arranged to be rolled around themselves with the supporting structure attached. Such as the rolling motion described above with references to FIGS. 22 and 23, the frame may be rolled so as to wrap or unwrap layers of supporting structure around the frame. Advantageously, this can allow for the selective tensioning of the supporting structure. For example, a medical professional may roll a frame of a retractor in an inside-out direction so as to wrap portions of the supporting structure around the frame and increase the tension of the supporting structure extending across the central opening. Alternatively or additionally, the frame and supporting structure can be arranged so that the frame can be rolled independently of the supporting structure. For example, the supporting structure may loop around a portion of the frame and allow the frame to be rolled, such as to face a desired surface of the frame away from the central opening, without wrapping additional portions of the supporting structure around the frame.

Method of Construction

In one embodiment, the method may begin by a manufacturer obtaining materials to form the frame and the supporting structure and/or determining the desired shape and size of the retractor. In some instances, a frame member, such as an elastomeric extrusion, is cut to an appropriate length for the size and shape of the retractor desired to be constructed. Similarly, in some cases, the supporting structure, such as a monolithic polymeric web material, may be cut into a desired shape for the retractor. After obtaining the frame member and the supporting structure, the frame can be passed and/or weaved through the openings defined by the supporting structure. For example, a first end of the extrusion can be passed back and forth through openings along the perimeter of the supporting structure so as to form a woven configuration.

After positioning the frame member around a portion of the supporting structure, the first and second ends of the frame can brought into close proximity to one another and be coupled to one another such as by solvent-bonding and/or use of an end-region coupling member, such as that illustrated in FIG. 4. Once the retractor is assembled the product may be packaged such as by packaging the retractor in a kit and/or within a sterile package for distribution to sales persons, distributors, hospitals and/or medical professionals.

Other arrangements of the above method are contemplated. In some instances, multiple processes may be performed simultaneously. For example, the frame and supporting structure may be sized and shaped simultaneously. Additionally or alternatively, stages/steps may be performed in a different order than that described above. For example, weaving the frame through the supporting structure may take place prior to cutting the frame and/or the supporting structure to its/their final size. This may be done by passing/weaving the frame member through openings in the supporting structure along a predetermined path and then cutting the excess frame member and portions of supporting structure that extend beyond the outer perimeter of the frame.

Method of Use

A method of using the above described embodiments of retractors may be initiated by obtaining measurements of the patient and selecting an embodiment of the inventive device, such as one sized to fit the patient. For example, a medical professional may select the arrangement of retractor such as the size and/or shape of the frame and/or the size, shape and/or configuration of openings defined by the supporting structure of the retractor based on the patient's anatomy, the procedure being performed, and/or other considerations of the medical professional.

In some instances, the medical professional configures the selected retractor into an insertable configuration such as by flattening the retractor upon itself to lower the profile of the retractor. For example, the medical professional may bend and/or twist the retractor into a smaller configuration. In some instances, the retractor is provided in the insertable configuration and no or minimal manipulation by the medical professional is necessary prior to insertion. The medical professional may then insert the retractor into the abdominal cavity of the patient in its insertable configuration. For example, the retractor can be introduced through a trocar or incision, and placed inside the abdominal cavity.

After the retractor has been inserted into the abdominal cavity and optionally while the retractor is still within the insertable configuration, the medical professional may position the retractor within the abdominal cavity such that when the retractor is deployed the retractor forms a working space in the desired location. For example, the device can be manipulated manually or via instruments, to position the perimeter frame in such a way that after upon deployment it will wedge itself against the front and back abdominal walls, and the supporting structure resist the bowel from passing from one side of the frame to the other.

When the retractor is in the desired position, the retractor is selectively deployed within the abdominal cavity, so as to configure the retractor from the insertable configuration into an expanded configuration arranged to retain organs and tissue of the patient from entering the working space during the procedures. Optionally, one or more sutures may be used to secure the retractor in position. The method of using a retractor may conclude by severing any sutures and configuring the retractor into an insertable configuration and removing the retractor from the patient and/or disposing of the retractor after satisfactory completion of the surgical procedure. For example, the frame may be flattened upon itself to lower its profile, and the device removed via a sufficiently sized incision/opening.

Other arrangements of the above method are contemplated. In some instances, multiple steps may be performed simultaneously. For example, the steps of inserting the retractor into the abdominal cavity of a patient and positioning the retractor within the abdominal cavity may be performed simultaneously. Additionally or alternatively, the above described steps may be performed in a different order than that discussed. For example, the step of configuring the retractor into an insertable configuration may be performed prior to selecting the retractor, such as by the retractor being packaged in the insertable configuration, so that the selected retractor is ready for insertion into the patient and requires no further preparation by a medical professional.

While at least one embodiment has been illustrated and described in detail in the drawings and foregoing description, the same is to be considered as illustrative and not restrictive in character, it being understood that the preferred embodiment has been shown and described and that all changes, equivalents, and modifications that come within the spirit of the inventions defined by following claims are desired to be protected. It will be evident from the specification that aspects or features discussed in one context or embodiment will be applicable in other contexts or embodiments. All publications, patents, and patent applications cited in this specification are herein incorporated by refer-

The invention claimed is:

1. A surgical retractor for insertion into a body of a patient, comprising:
a frame defining a central opening; and
a supporting structure extending across at least a portion of said central opening and comprising a series of intersecting strands defining strand openings therebetween;
wherein said strand openings are enlargeable by slidable passage of said strands relative to one another;
wherein the frame has an inward facing side facing the central opening and an opposing outward facing side facing away from the central opening;
wherein strands of the supporting structure extend around the frame and cover portions of the outward facing side of the frame;
wherein exposed portions of the outward facing side of the frame occur between covered portions such that an outer perimeter of the surgical retractor comprises alternating exposed portions and covered portions of the frame; and
wherein strands on the outward facing side of the frame extend a height above the exposed portions of the frame sufficient to provide traction between the surgical retractor and tissue of the patient when the surgical retractor is positioned inside the body of a patient.

2. The surgical retractor of claim 1, wherein:
said frame is deformably resilient.

3. The surgical retractor of claim 1, wherein:
said intersecting strands are interwoven.

4. The surgical retractor of claim 1, wherein:
said strands of said supporting structure are movable with respect to one another so as to change the arrangement of said strand openings.

5. The surgical retractor of claim 1, wherein:
at least one strand has a cross-section that changes along a length of said strand.

6. The surgical retractor of claim 1, wherein:
said strands are configurable to change the shape of said strand openings.

7. The surgical retractor of claim 1, wherein:
said frame extends through a plurality of said strand openings.

8. The surgical retractor of claim 7, wherein:
said frame is woven through a plurality of said strand openings.

9. The surgical retractor of claim 1, wherein:
slidable passage of said strands relative to one another enlarges one or more strand openings and shrinks or eliminates adjacent strand openings.

10. A surgical retractor, comprising:
a frame defining a central opening; and
a supporting structure extending across said central opening and comprising a web member defining web openings;
wherein said frame extends through a plurality of said web openings; wherein the frame has an inward facing side facing the central opening and an opposing outward facing side facing away from the central opening;
wherein the web member extends around the frame and covers portions of the outward facing side of the frame;
wherein exposed portions of the outward facing side of the frame occur between covered portions such that an outer perimeter of the surgical retractor comprises alternating exposed portions and covered portions of the frame; and
wherein the web member on the outward facing side of the frame extends a height above the exposed portions of the frame sufficient to provide traction between the surgical retractor and tissue of the patient when the surgical retractor is positioned inside the body of a patient.

11. The surgical retractor of claim 10, wherein:
said frame is deformably resilient.

12. The surgical retractor of claim 10, wherein:
said frame is woven through a plurality of said web openings.

13. The surgical retractor of claim 10, wherein:
said web member is configurable to change the size of said web openings.

14. The surgical retractor of claim 10, wherein:
said web member is configurable to change the shape of said web openings.

15. A surgical retractor, comprising:
a frame defining a central opening; and
a web member extending across at least a portion of said central opening and defining a plurality of web openings;
wherein said web member comprises a monolithic polymeric structure defining a plurality of intersecting struts forming said web member;
wherein the frame has an inward facing side facing the central opening and an opposing outward facing side facing away from the central opening;
wherein struts of the web member cover portions of the outward facing side of the frame;
wherein exposed portions of the outward facing side of the frame occur between covered portions such that an outer perimeter of the surgical retractor comprises alternating exposed portions and covered portions of the frame; and
wherein the struts on the outward facing side of the frame extend a height above the exposed portions of the frame sufficient to provide traction between the surgical retractor and tissue of the patient when the surgical retractor is positioned inside the body of a patient.

16. The surgical retractor of claim 15, wherein:
said frame is deformably resilient.

17. The surgical retractor of claim 15, wherein:
said frame is woven through a plurality of said web openings.

18. The surgical retractor of claim 15, wherein:
said web member comprises openings of less than approximately 1 inch in width.

19. The surgical retractor of claim 15, wherein:
said web member is free of knots.

20. The surgical retractor of claim 15, wherein:
said web member is flexibly resilient.

* * * * *